(12) United States Patent
Clough et al.

(10) Patent No.: US 8,809,568 B2
(45) Date of Patent: Aug. 19, 2014

(54) SYNTHESIS OF SILYLACETYLENES

(75) Inventors: Robert S. Clough, St. Paul, MN (US); John E. Anthony, Lexington, KY (US); Marcia M. Payne, Lexington, KY (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/639,873

(22) PCT Filed: May 25, 2011

(86) PCT No.: PCT/US2011/037854
§ 371 (c)(1),
(2), (4) Date: Oct. 8, 2012

(87) PCT Pub. No.: WO2011/150020
PCT Pub. Date: Dec. 1, 2011

(65) Prior Publication Data
US 2013/0060059 A1  Mar. 7, 2013

Related U.S. Application Data

(60) Provisional application No. 61/349,383, filed on May 28, 2010.

(51) Int. Cl.
C07F 7/02 (2006.01)

(52) U.S. Cl.
USPC ........... 556/476; 556/477; 556/478; 556/480; 556/481

(58) Field of Classification Search
CPC .......... C07F 7/123; C07F 7/16; C07F 7/0883; C07F 7/0896; C07F 7/12; C07F 7/122; C07F 7/08; C07F 7/083; C07F 7/0861; C07F 7/14; C07F 7/1876; C07F 7/0829; C07F 7/0827; C07F 7/125; C07F 7/0867; C07C 45/62; C07C 51/36; C07C 5/03; C07C 5/08; C07C 5/09
USPC ........................ 556/476, 478, 477, 480, 481
See application file for complete search history.

(56) References Cited

U.S. PATENT DOCUMENTS

| | | | |
|---|---|---|---|
| 5,068,368 | A | 11/1991 | Smith |
| 5,196,138 | A | 3/1993 | Smith |
| 5,342,984 | A | 8/1994 | Kubota |
| 6,690,029 | B1 | 2/2004 | Anthony |
| 7,576,208 | B2 | 8/2009 | Brown |
| 2006/0220007 | A1 | 10/2006 | Bailey |
| 2007/0137520 | A1 | 6/2007 | Brown |
| 2008/0191199 | A1 | 8/2008 | Anemian |
| 2008/0197325 | A1 | 8/2008 | Leeming |

FOREIGN PATENT DOCUMENTS

| | | |
|---|---|---|
| JP | 7252271 | 10/1995 |
| WO | WO 2005-055248 | 6/2005 |
| WO | WO 2006-119853 | 11/2006 |
| WO | WO 2008-128618 | 10/2008 |
| WO | WO 2009-079150 | 6/2009 |
| WO | WO 2009-155106 | 12/2009 |
| WO | WO 2010-138807 | 12/2010 |
| WO | WO 2011-149735 | 12/2011 |

OTHER PUBLICATIONS

Iwata; Journal of Organometallic Chemistry, 667, 2003, 90-95.*
Corriu, "(Ethynylhydrosilane) cobalt Carbonyl Complexes. Reactivity of the Silicon-Hydrogen Bond", *Organometallics*, vol. 9, 1990, pp. 2086-2091.
Haddon, "Band Electronic Structure of One- and Two-Dimensional Pentacene Molecular Crystals", *J. Phys. Chem. B*, 2002, vol. 106, pp. 8288-8292.
Hoffmann, "Selective Synthesis of Functional Alkynylmono- and -trisilanes", *Eur. J. Inorg. Chem*, vol. 7, 2010, pp. 1133-1142.
Iwata, $PdCl_2$ and $NiCl_2$-catalyzed hydrogen-halogen exchange for the convenient preparation of bromo- and iodosilanes and germanes, *Journal of Organometallic Chemistry*, vol. 667, 2003, pp. 90-95.
Midland, "Preparation and Use of Lithium Acetylide: 1-Methyl-2-Ethynyl-endo-3,3-Dimthyl-2-Norbornanol", *Organic Syntheses*, 1990, Coll., vol. 68, p. 14; and 1993, Coll. vol. 8, p. 391 (1993).
Tanino, "Synthesis of cyclic allenylsilanes via an intramolecular substitution reaction of 1-siloxy-2, 3-epoxyalkanes", *Tetrahedron Letter*, Elsevier, Amsterdam, NL, 2000, vol. 41, No. 48, pp. 9281-9285.
Troisi, "Electronic Interactions and Thermal Disorder in Molecular Crystals Containing Cofacial Pentacene Units", *Chem. Mater.*, 2005, vol. 17, pp. 5024-5031.
Wander, "Synthesis of Polyaryl Rigid-Core Carbosilane Dendrimers for Supported Organic Synthesis", *Organometallics*, 2009, vol. 28, pp. 4406-4415.
Wrackmeyer, "1-Silacyclopent-2-enes and 1-silacyclohex-2-enes bearing functionally substituted silyl groups in 2-positions. Novel electron-deficient Si-H-B bridges", *Applied Organometallic Chemistry*, 2006, vol. 20, pp. 99-105. [Published online Nov. 21, 2005 in Wiley InterScience (www.interscience.wiley.com). DOI:10.1002/aoc.1020.
International Search Report for PCT/US2011/037854, Mailed Aug. 11, 2011, 4 pages.

* cited by examiner

*Primary Examiner* — Sudhakar Katakam
*Assistant Examiner* — Pancham Bakshi
(74) *Attorney, Agent, or Firm* — Kent S. Kokko

(57) ABSTRACT

The present disclosure provides a method of preparing silylethynyl compounds in which two of the hydrocarbyl groups bonded to the silicon exclusive of the ethynyl group, are the same and one is different, that may be used in preparing novel silylethynyl functionalized acene semiconductor chromophores.

10 Claims, No Drawings

SYNTHESIS OF SILYLACETYLENES

CROSS REFERENCE TO RELATED APPLICATION

This application claims the benefit of U.S. Provisional Patent Application No. 61/349,383, filed May 28, 2010, the disclosure of which is incorporated by reference herein in its entirety.

BACKGROUND

Acenes, as a class of graphite substructures, are particularly attractive targets in the synthesis of organic semiconductors because of their demonstrated high mobilities, strong intermolecular coupling and small reorganization energies. The usefulness of acene oligomers such as pentacenes are already showing in numerous electronics applications including, but not limited to, thin-film transistors (display technologies), photovoltaic cells and light-emitting diodes.

Substituted acenes have received limited attention due to their synthetic inaccessibility. More specifically, while the properties and limitations of simple, linear conjugated organic systems have been well studied by either synthesis or structure-property determinations performed on series of oligomers, few such studies have been performed on fused aromatic systems, simply because of a lack of synthetic methodology available for their preparation. Although a number of researchers have made excellent approaches to planarized graphitic oligomers and polymers, and simple fused aromatic systems based on the graphite lattice are already being explored for the construction of field effect transistors (FETs) and molecular electronic devices, the lack of a reliable route to synthetically-tailored linearly fused aromatics has precluded the development of fully tunable organic materials.

The ability to tailor organic materials to maximize film-forming abilities or solid-state order cannot be understated, as such customization will allow the use of such systems as components for RFID tags, flexible displays, light-weight solar panels and ubiquitous semiconductor electronics. Functionalization is critical to enable exploration of self-organization in these graphite-like systems. Pendant groups on an oligoacene can be used to alter the solubility, stability and solid-state ordering of the material. Numerous studies of organic semiconductors, including band structure and exchange integral calculations, have shown that subtle changes in semiconductor crystal packing in systems such as the silylethyne-substituted acenes can yield dramatic increases in mobility. See J. E. Anthony et al., *J. Phys. Chem. B*, 2002, 106, 8288; and J. E. Anthony, et al, *Chem. Mater.* 2005, 17, 5024.

A number of attempts at modification of packing in current high-performance semiconductors have indeed shown such improvements; for example, alkylation of pentacene, or halogenation of anthradithiophene chromophores led to changes in crystallization or crystal packing that improved performance relative to the parent hydrocarbon. Unfortunately, these approaches require significant additional synthesis steps, and reduce the low-cost advantage promised by organic semiconductors.

SUMMARY

The present disclosure provides a method of preparing silylethynyl compounds in which two of the hydrocarbyl groups bonded to the silicon are the same and one is different exclusive of the ethynyl, which may be used in preparing novel silylethynyl functionalized acene semiconductor chromophores. The silylethyne approach to functionalizing semiconductor chromophores allows straightforward engineering of solid-state order by the simple alteration of the trialkylsilyl substituent. Changes in the groups on the silane yield a variety of pi-stacked structures, and for compounds of similar pi-stacked structure, such as one-dimensional pi-stacked materials, changes to the trialkylsilyl groups have yielded dramatically different thermal properties. Further investigation of the effect of the trialkylsilyl groups on the properties and electronic performance of the silylethynyl functionalized acenes have been hampered by the absence of versatile, efficient synthetic approaches to unsymmetrical silyl acetylenes, i.e. silyl acetylenes in which the three substituents on the silicon other than the ethynyl or acetylene group are not identical.

The present disclosure provides an improved method of preparing silyl acetylenes (also referred to as ethynylsilane or silylethynl compounds), in which two of the hydrocarbyl groups bonded to the silicon are the same and one is different, that may be used in preparing novel silylethynyl functionalized acenes using the methods described in WO 2009/155106 (Anthony et al.). Such compounds are of the formula

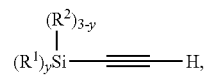

where $R^1$ and $R^2$ are (hetero)hydrocarbyl groups, and $R^1$ is not $R^2$, and y is 1 or 2.

The method provides silyl acetylenes of higher purity in a more economical manner. Purity of the silyl acetylene is important as it impacts the purity of the silylethynyl functionalized acene, and thus can dictate the purification process required to afford high purity acenes for use in electronic devices. Small levels of impurities in the silylethynyl functionalized acene semiconductors can be detrimental to electronic performance characteristics such as charge carrier mobility, ON/OFF current ratio, and OFF current, and can effect device stability.

The ability to tailor organic materials to maximize film-forming abilities or solid-state order cannot be understated, as such customization will allow the use of such materials in low-cost or large-area electronics (e.g. RFID tags), as the backplane in flexible flat-panel displays or as donors or acceptors in solar panels. Functionalization will also allow the exploration of self-organization in these graphite-like systems. Pendant groups on an oligoacene can be used to alter the solubility, stability and solid-state ordering of the material.

The instant method provides silylethynyl compounds that enable the further preparation of functionalized acene compounds which, in turn, influence the processability, solid-state order and stability of the resulting material, and in many embodiments, improved electronic properties.

As used herein:

"Alkyl" refers to a monovalent group that is a radical of an alkane, which is a saturated hydrocarbon. The alkyl can be linear, branched, cyclic, or combinations thereof and typically contains 1 to 30 carbon atoms. In some embodiments, the alkyl group contains 1 to 30, 1 to 20, 4 to 20, 1 to 14, 1 to 10, 4 to 10, 4 to 8, 1 to 8, 1 to 6, or 1 to 4 carbon atoms. Examples of alkyl groups include, but are not limited to, methyl, ethyl, n-propyl, iso-propyl, cyclopropyl, n-butyl, tert-butyl, iso-butyl, n-pentyl, n-hexyl, cyclohexyl, n-octyl, n-heptyl, and ethylhexyl.

"Alkenyl" refers to a monovalent group that is a radical of an alkene, which is a hydrocarbon with at least one carbon-carbon double bond. The alkenyl can be linear, branched, cyclic, or combinations thereof and typically contains 2 to 30 carbon atoms. In some embodiments, the alkenyl contains 2 to 20, 2 to 14, 2 to 10, 4 to 10, 4 to 8, 2 to 8, 2 to 6, or 2 to 4 carbon atoms. Exemplary alkenyl groups include ethenyl, propenyl, isopropenyl, allyl, and 2-but-1-enyl.

"Alkynyl" refers to a monovalent group that is a radical of an alkyne, a hydrocarbon with at least one carbon-carbon triple bond. The alkynyl can be linear, branched, cyclic, or combinations thereof and typically contains 2 to 30 carbon atoms. In some embodiments, the alkynyl contains 2 to 20, 2 to 14, 2 to 10, 4 to 10, 4 to 8, 2 to 8, 2 to 6, or 2 to 4 carbon atoms. Exemplary alkynyl groups include ethynyl, propynyl, and butynyl. Some alkynyl groups such as an ethynyl can be further substituted with a silyl group.

"Aryl" refers to a monovalent group that is a radical of an aromatic carbocyclic compound. The aryl can have one aromatic ring or can include up to 5 carbocyclic ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

"Aralkyl" refers to an alkyl substituted with an aryl group.

"Halo" refers to a halogen group (i.e., —F, —Cl, —Br, or —I).

"Haloalkyl" refers to an alkyl that is substituted with one or more halo groups.

"heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent.

"(hetero)alkyl" includes both alkyl and heteroalkyl.

"heteroaryl" is aryl containing 1-3 heteroatoms such as nitrogen, oxygen, or sulfur and can contain fused rings. Some examples of heteroaryl groups are pyridinyl, furanyl, pyrrolyl, thienyl, thiazolyl, oxazolyl, imidazolyl, indolyl, benzofuranyl, and benzthiazolyl.

"(hetero)aryl" includes both "heteroaryl" and aryl.

"hydrocarbyl" refers to groups containing only hydrogen and carbon, including cyclic or acyclic alkyl, alkenyl, alkynyl, and aryl groups.

As used herein, "(hetero)hydrocarbyl" is inclusive of hydrocarbyl alkyl and aryl groups, and heterohydrocarbyl heteroalkyl and heteroaryl groups, the later comprising one or more catenary oxygen heteroatoms such as ether or amino groups. Heterohydrocarbyl may optionally contain one or more catenary (in-chain) functional groups including ester, amide, urea, urethane, sulfonamide and carbonate functional groups. Unless otherwise indicated, the non-polymeric (hetero)hydrocarbyl groups typically contain from 1 to 60 carbon atoms.

"Silylethynyl" refers to a monovalent group of formula —C≡C—Si(R$^a$)$_3$ where R$^a$ is independently selected from hydrogen, alkyl, alkoxy, alkenyl, heteroalkyl, hydroxyalkyl, aryl, aralkyl, heteroaryl, or heteroaralkyl. These groups are sometimes referred to as silanylethynyl groups.

DETAILED DESCRIPTION

In the method of this disclosure, a halohydrocarbylsilane of formula I is provided

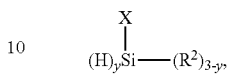

I where X is a halogen atom or other suitable leaving groups such as a triflate, preferably Cl or Br, and R$^2$ is a (hetero)hydrocarbyl group, preferably a hydrocarbyl group and more preferably an alkyl group, including cycloalkyl group, or an alkenyl group and y is 1 or 2. Such compounds are readily prepared e.g. by the partial hydrosilylation of chlorosilane, or partial alkylation of e.g. trichlorosilane, and many are commercially available, including halo(di)isopropylsilane and (di)allyl halosilane.

The halo compound of Formula I may be ethynylated to the desired silylethynyl compound by nucleophilic displacement of the halide by an acetylide to produce compound of Formula II.

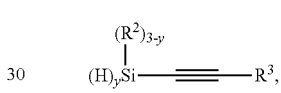

II where R$^2$ are (hetero)hydrocarbyl groups, R$^3$ is H or an acetylene-protecting group and y is 1 or 2.

More specifically, the compound of Formula I may be reacted with an alkali- or alkali earth metal acetylide of the formula

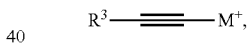

where M+ is an alkali- or alkali earth metal cation, including Grignard regents, and R$^3$ is H— or an acetylene protecting group such as (CH$_3$)$_3$—Si—.

The term "protecting group" refers to any group which when bound to one or more ethynyl groups of the compounds described herein will prevent reactions from occurring at these protected functionalities and which protecting group can be removed by conventional chemical steps to reestablish the unprotected ethynyl functional group. The particular removable blocking group employed is significant, as it must be selectively removed in the presence of the desired silyl group. Suitable protecting groups for various functional groups as well as suitable conditions for protecting and deprotecting particular functional groups are well known in the art. For example, numerous protecting groups are described in W. Greene and P. G. M. Wuts, Protecting Groups in Organic Synthesis, Third Edition, Wiley, New York, 1999, and references cited therein.

Preferably the ethynyl protecting groups is selected from lower trialkylsilanes such as trimethylsilyl, (3-cyanopropyl)dimethylsilyl, triethylsilyl, t-butyldimethylsilyl, hexyldimethylsilyl, benzyldimethylsilyl, dimethyl[1,1-dimethyl-3-(tetrahydro-2H-pyran-2-yloxy)propylsilyl, biphenyldimethylsilyl, methylol, —CHO, and —CH(OCH$_3$)$_2$. Such protecting groups may be subsequently removed by methods known in the art including treatments with dilute base or fluoride ion.

The acetylide may be prepared by techniques know in the art. For example, it may be prepared by reacting the acetylene compound with a lithium alkyl or lithium amide reagent. Such methods are described, for example in Organic Syntheses, Coll. Vol. 8, p. 391 (1993); Vol. 68, p. 14 (1990), and U.S. Pat. Nos. 5,068,368 or 5,196,138 (Smith et al.). The acetylide so generated is then contacted with the halo compound of Formula I.

In embodiments where $R^3$=H, the acetylide may be prepared in situ by bubbling acetylene gas though a solution or suspension of an alkyl lithium or lithium amide compound in an inert solvent. Alternatively, ethynylmagnesium bromide (ethynyl Grignard) can be purchased as a commercial solution from a number of vendors (including Sigma-Aldrich).

Compounds of Formula II are then subjected to a hydrogen-bromine exchange reaction using a group 10 transition metal catalyst in the presence of an alkyl or alkylene bromide compound to convert the hydrosilane to a bromosilane. Such transition metal mediated exchange reactions were found to provide high yields of the desired bromosilane or silyl bromide, minimal byproducts, and the catalyst residue was easily separated from the product. Other methods for effecting this conversion, such as the use of the brominating agents N-bromosuccinimide or bromine afforded more byproducts and often decreased yields The Group 10 catalyst used in this reaction may be metal palladium, platinum or nickel. The catalyst may be, in addition to the zero valent metal, salts such as chlorides, acetates, propionate and bisacetylacetonatopalladium; and metal complexes such as benzonitrile complexes, acetonitrile complexes, and triphenylphosphine complexes. In principle, this reaction does not require the use of any reaction solvent, but aprotic reaction solvents such as tetrahydrofuran, benzene toluene and decalin may be used in the reaction If zero valent metal catalyst is used, it is preferably used in the form of powder because of its high surface area and, in particular, the metal catalyst is used in the form of an active carbon- or alumina-supported catalyst since it can easily be handled.

The hydrogen-bromine transition metal catalyst mediated exchange takes place in the presence of an aliphatic bromide, including alkyl and alkenyl bromides. Specific example of aliphatic bromides include methyl bromide, ethyl bromide, n- and iso-propyl bromide, n-, sec- and isobutyl bromide, allyl bromide, methallyl bromide, 3-bromo-1-butene, and 1-bromo-3-pentene.

The amount of the aliphatic bromide reacted with the trihydrocarbylsilane of Formula II ranges from 1 to 2 times the equivalent amount of the latter. The amount of the catalyst used in the reaction ranges from 1 to 10000 ppm and preferably 10 to 1000 ppm on the basis of the amount of the trihydrocarbylsilane.

The reaction is carried out at a temperature preferably ranging from 40 to 150° C. and is generally conducted under an inert atmosphere.

Specifically, the foregoing reaction permits the preparation of compounds of the formula III:

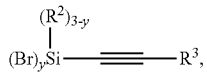
III where $R^1$ and $R^2$ are (hetero)hydrocarbyl groups, $R^1$ is not $R^2$, $R^3$ is an acetylene-protecting group and y is 1 or 2.

Compounds of Formula III are then reacted, in a suitable solvent, with an organometallic reagent of the formula:

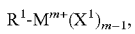

wherein $M^{m+}$ an alkali- or alkali earth metal cation of valence m, where m is 1 or 2, $X^1$ is a halide, and y is 1 or 2.

$R^1$ is selected to be different from $R^2$ as trihydrocarbylsilyl halides, with three identical hydrocarbyl groups, are more available and may be prepared by a variety of different methods. Preferably $R^1$ is selected from an alkyl, aryl or alkenyl group. To the availability and/or ease of preparation, organometallic reagent is a Grignard reagent, or a organolithium reagent.

Representative examples of organometallic reagents that are suitable for use in the process of this invention are methylmagnesium halide, ethylmagnesium halide, n-propylmagnesium halide, isopropenylmagnesium halide, n-butylmagnesium halide, butenylmagnesium halide, n-hexylmagnesium halide, tetramethylenedimagnesium dihalide, n-octylmagnesium halide, phenylmagnesium halide, adamantylmagnesium halide, 1-tetradecylmagnesium halide, 3-methylbenzylmagnesium halide, crotylmagnesium halide, 4-hexadecylphenylmagnesium halide, vinylmagnesium halide, allylmagnesium halide and cyclpropoylmagnesium halide. Preferably the halide is bromide or chloride or iodide. Further, propyllithium, cyclopropyllithium, vinyllithium, propenyllithium, allyllithium, isopropenyllithium, and butenyllithium are examples of organolithium reagents that might be selected for addition to the halosilane. As would be understood by one skilled in the art, other corresponding alkali metal compounds could also be used.

Stoichiometric amounts of the organometallic reagent are preferably used in this reaction. However, an excess of up to 200 mole percent of the organometallic reagent, with a preferred excess of up to 100 mole percent, and a more preferred excess of 5 to 25 mole percent, can be employed, relative to the molar equivalents of the bromide.

Suitable solvents include hexanes, heptanes, tetrahydrofuran, 1,2-dimethoxyethane, and ether, for example. The aforesaid reaction is typically run for a period of time from 0.5 hours to 48 hours, generally 1 hour, at a temperature from −78 to 40° C., generally from −78 to 0° C. The aforesaid reaction is typically run for a period of time from minutes to several hours to 48 hours, generally 1 hour.

The product of the above reaction is of is of the formula:

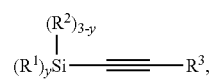
IV where $R^1$ and $R^2$ are (hetero)hydrocarbyl groups, and $R^1$ is not $R^2$, $R^3$ is H or an acetylene-protecting group, and y is 1 or 2.

If present, the protecting group $R^3$ of the compounds of Formula IV is then removed by means known in the art. In embodiments where $R^3$ is $(CH_3)_3$—Si—, the product may be desilylated by contacting with a suitable desilylating agent. Such desilylating reagents include catalytic amounts (5% to 10%, mol:mol) of fluoride compounds, or dilute base (such as sodium hydroxide, potassium hydroxide, potassium carbonate) in an alcoholic solvent, or an alcoholic solvent with a solubilizing co-solvent such as tetrahydrofuran or diethyl ether or other desilylating reagents described in Greene and Wuts, "Protecting Groups in Organic Synthesis," (John Wiley & Son Press, 2nd Ed) may be employed. Suitable solvents include ether, tetrahydrofuran, dichloromethane, ethanol, methanol and toluene, for example. The aforesaid reaction is run for a period of time from 0.5 hours to 5 hours, generally 1 hour, at a temperature from 0 to 40° C. generally from 10 to 25° C.

EXAMPLES

All parts, percentages, ratios, etc. in the examples are by weight, unless noted otherwise. Solvents and other reagents used were obtained from Sigma-Aldrich Chemical Company; Milwaukee, Wis. unless specified differently.
Materials
Trimethylsilylacetylene was obtained from GFS Chemicals, Powell, Ohio.
Diisopropylchlorosilane was obtained from Gelest, Inc., Morrisville, Pa.
Pentane, hexanes, dichloromethane, acetone, and methanol were obtained from Pharmco-Aaper, Brookfield, Conn.
Tetrahydrofuran (THF) (anhydrous, ≥99.9%, inhibitor free) was obtained from Sigma Aldrich Chemical Company, Milwaukee, Wis.
Silica gel (60 Å, 32-63 μm) was obtained from Sorbent Technologies, Atlanta, Ga.
Magnesium sulfate (anhydrous $MgSO_4$) and sodium hydroxide were obtained from Mallinckrodt Baker Inc., Philipsburg, N.J.
Test Methods
$^1$H NMR spectra were recorded on Varian (Unity 400 MHz) spectrometer (available from Varian, Inc., Palo Alto, Calif.) with tetramethylsilane as internal standard.
Mass spectral analyses were performed in Electron Ionization (EI) mode on a JEOL (JMS-700T) mass spectrometer (available from JEOL Ltd., Tokyo Japan).

Example 1

Synthesis of (Allyldiisopropylsilyl)acetylene

Synthesis of (Trimethylsilylethynyl)diisopropylsilane

In an oven-dried flask, trimethylsilylacetylene (7.02 g, 71.5 mmol) was dissolved in pentane (60 mL), and cooled to 0° C. in an ice bath. n-Butyllithium (26 mL, 2.5 M in hexanes, 65 mmol,) was added dropwise and the temperature was maintained for an hour. Diisopropylchlorosilane (10.0 g, 66.4 mmol) was added slowly, and the suspension was allowed to warm overnight. The reaction was quenched by the addition of water (60 mL) and stirred until all precipitate dissolved. The organic layer was separated, and the aqueous layer was extracted with pentane (40 mL). The organic layers were combined, washed with water (2×20 mL), and dried over magnesium sulfate. The resulting solution was rinsed onto a thin pad of silica and the product was eluted with additional pentane. Solvent was carefully removed from the volatile desired product using a rotary evaporator to yield 14 g (66 mmol, 99%) of a colorless liquid. $^1$H-NMR (400 MHz, $CDCl_3$) δ=3.6 (s, 1H), 1.0 (m, 14H), 0.1 (s, 9H).

Synthesis of (Trimethylsilylethynyl)diisopropylbromosilane (Trimethylsilylethynyl)diisopropylsilane (14 g, 66 mmol) and allyl bromide (~40 mL) were added to a round-bottom flask equipped with a stir-bar. A septum and bubbler were attached and the solution was purged with $N_2$ for 15 min. $PdCl_2$ (0.06 g, 0.3 mmol, 0.5 mol %) was added and the reaction was heated at 60° C. for 3 hours, or until analysis by GC-MS showed complete conversion to the bromide. After removing the reaction from the heat, pentane (50 mL) was added and the solution was chilled for 20 min. The $PdCl_2$ was removed by filtration through a fine fitted funnel, then solvent was removed using a rotary evaporator, yielding 18.8 g of (trimethylsilylethynyl)diisopropylbromosilane as a light brown liquid.

Synthesis of (Allyldiisopropylsilyl)acetylene

The (trimethylsilylethynyl)diisopropylbromosilane intermediate was transferred to an oven-dried flask, dissolved in anhydrous THF, treated with 1.2 equivalents of allylmagnesium chloride (2.0 M in THF) dropwise, and heated to 45° C. for 12 hrs. The reaction was quenched by the slow addition of ice water, then dilute sulfuric acid to dissolve magnesium salts, followed by the addition of pentane. The organic layer was separated, and the aqueous layer was extracted with pentane one additional time. Organic layers were combined, washed with water and brine, dried over magnesium sulfate, filtered, and concentrated under rotary evaporation. Removal of the trimethylsilyl substituent is effected by treatment with 6-8 drops of 15% NaOH in 1:1 THF:MeOH, followed by stirring for 1-2 hours. Analysis by GC-MS was helpful to ascertain completion of the deprotection, since thin layer chromatography (hexanes, visualization by potassium permanganate stain) revealed no appreciable difference between the trimethylsilyl-protected and deprotected acetylene. The product was isolated by extraction into hexanes (2×50 mL). The organic layer was washed with 10% HCl (10 mL) and water (2×10 mL), then dried over magnesium sulfate, filtered, and concentrated under rotary evaporation to yield 11.3 g of crude (allyldiisopropylsilyl)acetylene.

Further purification by chromatography on silica gel with hexanes as eluant yielded 10.8 g pure (allyldiisopropylsilyl) acetylene (overall yield of 90.9% from the intermediate (trimethylsilylethynyl)diisopropylsilane) as a colorless liquid. $^1$H-NMR (200 MHz, $CDCl_3$) δ=5.9 (m, 1H), 4.9 (m, 2H), 2.4 (s, 1H), 1.7 (dt, J=1.4 Hz, 8 Hz, 2H), 1.1 (s, 14H).

The invention is illustrated with the following embodiments:
1. A process for preparing a compound of the formula

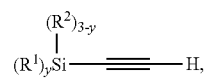

where $R^1$ and $R^2$ are (hetero)hydrocarbyl groups, and $R^1$ is not $R^2$, and y is 1 or 2,
comprising the steps of
a) contacting a hydrocarbylsilane of the formula

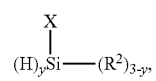

where
$R^2$ are (hetero)hydrocarbyl groups and X is a halogen atom;
with an with an organometallic reagent of the formula:

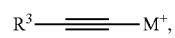

where M+ is an alkali- or alkali earth metal cation, $R^3$ is H— or an acetylene protecting group,
b) brominating the product of step a) with a transition metal bromination catalyst and an aliphatic bromo compound;

c) contacting the product of step b) with an organometallic compound of the formula $R^1\text{-}M^{m+}(X^1)_{m-1}$, wherein $M^{m+}$ an alkali- or alkali earth metal cation of valence m, where m is 1 or 2, $X^1$ is a halogen atom, and y is 1 or 2, and d) where $R^3$ is a protecting group, removing the acetylene protecting group $R^3$.

2. The process of embodiment 1, where each of $R^1$ and $R^2$ are selected from alkyl, alkenyl, cycloalkyl and aryl, or combinations thereof 3. The process of any the previous embodiments, where the transition metal bromination catalyst is a Group 10 transition metal halide and the aliphatic bromo compound is an alkyl- or allyl bromide.

4. The process of any the previous embodiments wherein said transition metal halide is $PdCl_2$ or $NiCl_2$.

5. The process of any the previous embodiments, where $R^3$ is $(CH_3)_3\text{—Si—}$.

6. The process of embodiment 5 where said step of removing the protecting group $R^3$ comprises treatment with an alcoholic base.

7. The process of any the previous embodiments wherein the product of step a) is of the formula:

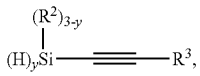

where $R^2$ are (hetero)hydrocarbyl groups, $R^3$ is H or an acetylene-protecting group and y is 1 or 2.

8. The process of any the previous embodiments wherein the product of step b) is of the formula:

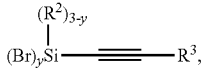

where $R^2$ are (hetero)hydrocarbyl groups, $R^3$ is H or an acetylene-protecting group and y is 1 or 2.

9. The process of any the previous embodiments wherein the product of step c) is of the formula:

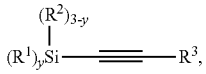

where $R^1$ and $R^2$ are (hetero)hydrocarbyl groups, and $R^1$ is not $R^2$, $R^3$ is H— or an acetylene-protecting group and y is 1 or 2.

10. The process of any the previous embodiments where $R^3$ is H— and $R^3\text{-}{\equiv}\text{-}M^+$ is generated in situ by contacting acetylene with an alkyl lithium compound.

What is claimed is:
1. A process for preparing a compound of the formula

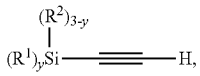

where $R^1$ and $R^2$ are (hetero)hydrocarbyl groups, and $R^1$ is not $R^2$, and y is 1 or 2, comprising the steps of a) contacting a hydrocarbylsilane of the formula

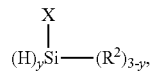

where $R^2$ are (hetero)hydrocarbyl groups and X is a halogen atom;

with an with an organometallic reagent of the formula:

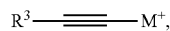

where M+ is an alkali- or alkali earth metal cation, $R^3$ is H— or an acetylene protecting group, b) brominating the product of step a) with a transition metal bromination catalyst and an aliphatic bromo compound;

c) contacting the product of step b) with an organometallic compound of the formula $R^1\text{-}M^{m+}(X^1)_{m-1}$, wherein $M^{m+}$ an alkali- or alkali earth metal cation of valence m, where m is 1 or 2, $X^1$ is a halogen atom, and y is 1 or 2, and d) where $R^3$ is a protecting group, removing the acetylene protecting group $R^3$.

2. The process of claim 1, where each of $R^1$ and $R^2$ are selected from alkyl, alkenyl, cycloalkyl and aryl, or combinations thereof.

3. The process of claim 1, where the transition metal bromination catalyst is a Group 10 transition metal halide and the aliphatic bromo compound is an alkyl- or allyl bromide.

4. The process of claim 3 wherein said transition metal halide is $PdCl_2$ or $NiCl_2$.

5. The process of claim 1, where $R^3$ is $(CH_3)_3\text{—Si—}$.

6. The process of claim 5 where said step of removing the protecting group $R^3$ comprises treatment with an alcoholic base.

7. The process of claim 1 wherein the product of step a) is of the formula:

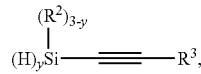

where $R^2$ are (hetero)hydrocarbyl groups, $R^3$ is H or an acetylene-protecting group and y is 1 or 2.

8. The process of claim 1 wherein the product of step b) is of the formula:

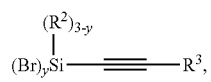

where $R^2$ are (hetero)hydrocarbyl groups, $R^3$ is H or an acetylene-protecting group and y is 1 or 2.

9. The process of claim 1 wherein the product of step c) is of the formula:
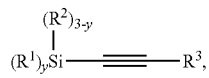
where $R^1$ and $R^2$ are (hetero)hydrocarbyl groups, and $R^1$ is not $R^2$, $R^3$ is H— or an acetylene-protecting group and y is 1 or 2.
10. The process of claim 1 where $R^3$ is H— and $R^3$-≡-$M^+$ is generated in situ by contacting acetylene with an alkyl lithium compound.
* * * * *

UNITED STATES PATENT AND TRADEMARK OFFICE
CERTIFICATE OF CORRECTION

PATENT NO. : 8,809,568 B2
APPLICATION NO. : 13/639873
DATED : August 19, 2014
INVENTOR(S) : Clough et al.

It is certified that error appears in the above-identified patent and that said Letters Patent is hereby corrected as shown below:

On the Title Page, item [54] and in the Specification, Column 1, Line 1, the title, delete "SYNTHESIS OF SILYLACETYLENES" and insert -- SYNTHESIS OF SILYL ACETYLENES --, therefor.

In the Specification

Column 2,
Line 19, delete "silylethynl" and insert -- silylethynyl --, therefor.

In the Claims

Column 9,
Line 10, Claim 2, delete "therefor" and insert -- therefor. --, therefor.

Signed and Sealed this
Sixteenth Day of December, 2014

Michelle K. Lee
*Deputy Director of the United States Patent and Trademark Office*